(12) United States Patent
Servidio (10) Patent No.: US 9,522,007 B2
(45) Date of Patent: Dec. 20, 2016

(54) ORTHOPEDIC SAW BLADE

(75) Inventor: Damon J. Servidio, Towaco, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 925 days.

(21) Appl. No.: 13/544,115

(22) Filed: Jul. 9, 2012

(65) Prior Publication Data

US 2014/0012265 A1 Jan. 9, 2014

(51) Int. Cl.
*A61B 17/00* (2006.01)
*A61B 17/14* (2006.01)

(52) U.S. Cl.
CPC .................................... *A61B 17/14* (2013.01)

(58) Field of Classification Search
CPC ....... A61B 17/141; A61B 17/148; B26B 9/00; B26B 9/02; B23D 61/006; B27C 5/10; B27G 17/00; B27G 17/02; B27G 17/025; B27G 17/04; B27G 17/06
USPC ..... 30/351, 355, 356; 83/835–855; 606/176, 606/178
See application file for complete search history.

(56) References Cited

U.S. PATENT DOCUMENTS

| | | | | |
|---|---|---|---|---|
| 1,328,547 | A * | 1/1920 | Shaw | B26B 9/00 30/115 |
| 2,431,235 | A * | 11/1947 | Flaa | 30/144 |
| 4,179,967 | A * | 12/1979 | Clark | B23D 61/12 83/661 |
| 5,694,693 | A * | 12/1997 | Hutchins et al. | 30/166.3 |
| 5,851,209 | A * | 12/1998 | Kummer et al. | 606/103 |
| 7,837,690 | B2 | 11/2010 | Metzger | |
| 9,027,452 | B2 * | 5/2015 | Nagy | B23D 61/006 30/348 |
| 2008/0009848 | A1 * | 1/2008 | Paraschiv et al. | 606/34 |
| 2008/0172892 | A1 * | 7/2008 | Henrickson | 30/392 |
| 2009/0312761 | A1 * | 12/2009 | Boykin et al. | 606/82 |
| 2011/0125174 | A1 * | 5/2011 | Babaev | 606/169 |

\* cited by examiner

*Primary Examiner* — Anu Ramana
(74) *Attorney, Agent, or Firm* — Lerner, David, Littenberg, Krumholz & Mentlik, LLP (57) ABSTRACT

A saw blade has a base configured for attachment with a driver, the saw being configured for cutting bone. The saw blade includes a body extending from the base to a free end, the body enclosing at least three sides of an open area adjacent the base. The blade further includes a cutting edge having a width and disposed on the body adjacent to the free end thereof and adjacent to the open area such that at least a portion of the cutting edge is disposed toward the base. The open area of the saw blade can be sized to receive a portion of a long bone therein.

16 Claims, 7 Drawing Sheets

FIG. 9

ORTHOPEDIC SAW BLADE

BACKGROUND OF THE INVENTION

The present disclosure relates to blades used in connection with saws during orthopedic procedures. The present disclosure also relates to methods for using such blades in orthopedic procedures.

Orthopedic saw blades are devices that cut bone and are structured to function appropriately under the conditions of orthopedic surgery. Many such saws include a driver or driver unit that includes a chuck or other attachment for securing a blade thereto. The driver is configured to move the saw blade in a desired motion to make a cut in a selected area of a bone. Often, such a motion involves oscillation of the saw blade through an arc that can be centered about the proximal portion of the saw blade. The proximal portion of the blade being configured for engagement with the chuck. Some drivers cause such motion by rotating the chuck itself about an axis normal to a plane along which the blade oscillates.

Saw blades can be structured to make contact with a bone to be cut through an incision while avoiding contact with the skin of the patient or other soft tissue surrounding the prepared area. Many saw blades can be of a long, narrow structure with a set of teeth extending across a distal end thereof, allowing them to reach a desired depth of cut from a straight-line approach through an incision.

Joint replacement or arthroplasty is a surgical procedure involving the removal of one or more articulating surfaces of bones in a joint that have become damaged. Such removal or resection is often completed using a surgical saw, which can further be used in connection with a cutting guide, as discussed above. Once the damaged articulating surface has been removed, a prosthesis that replicates the original anatomical structure is implanted in the joint by attachment to the bone. Many prosthesis include an anchoring feature that can extend into the cancellous bone near the center thereof. Such features can help secure the implant in place both during and after healing. For example, a femoral implant for a hip joint can include a stem that extends partially into the center of the femur. Similarly, tibial plateau implants for knee arthroplasty procedures can include one or more keels or fins that extend into the tibia along a medial-lateral width or an anterior-posterior length. Alternatively, a tibial plateau implant can include a number of smaller projections that extend into the tibia at various points within the resected area.

At times it may be necessary to replace a worn or damaged implant by what is known as a revision procedure. Such procedures involve removing the worn or damaged implant from the joint, preparing the area and installing the new implant. The implants to be removed are often cemented in place or are affixed to the bone in areas of the implant that allow for ingrowth of bone material during healing. Accordingly, the implant must be physically loosened or freed from the bone during removal. One way to loosen an implant is using an orthopedic saw. However, in some instances the presence of anchoring features can make loosening difficult because areas that need to be loosened can be on a side of the anchoring feature that is opposite the incision. This arrangement can block such areas from saw blades that require, for example, a straight-line approach. These and other similar difficulties have required larger than desired incisions or additional incisions to be made during, for example, knee and hip revision procedures. The use of saws for loosening implants can also necessitate excessive retraction of soft tissue or repositioning of soft tissue during a procedure. Accordingly, further advances in the area of orthopedic saw blades may be useful.

BRIEF SUMMARY OF THE INVENTION

An aspect of the present disclosure relates to a saw blade having a base configured for attachment with a driver, the saw being configured for cutting bone. The saw blade includes a body extending from the base to a free end, the body enclosing at least three sides of an open area adjacent the base. The blade further includes a cutting edge having a width and disposed on the body adjacent to the free end thereof and adjacent to the open area such that at least a portion of the cutting edge is disposed toward the base. The open area of the saw blade can be sized to receive a portion of a long bone therein.

The cutting edge can be aligned with a longitudinal axis of the base, and the width of the cutting edge can define a lateral axis of the cutting edge that is disposed at a first angle to the lateral axis. The first angle can be, for example, between 70° and 110°. In another example, the first angle can be about 90°.

The base of the saw blade can define a center of rotation for the blade, and the cutting edge can extend along a lateral axis thereof that is tangent to an arc centered at the point of rotation.

The body of the blade can include an arm that is disposed outside of the open area. The arm of the blade can have an inside edge, and the cutting edge can have an inside end disposed toward the inside edge of the arm and an outside end remote therefrom. The inside edge of the arm can be spaced apart from the inside end of the cutting edge at a first distance. The cutting edge can include a plurality of teeth having substantially equal widths that are spaced apart along the width of the cutting edge. In such an example, the first distance can be at least equal to the width of one of the teeth.

The base of the saw blade can define a centerline extending in the first direction, and the body can extend away from the attachment portion along an arced path having a first directional component that extends from the centerline to a first location remote therefrom and from the first location back to the centerline. The cutting edge can intersect the centerline. Further, the cutting edge can extend away from the centerline on a first side thereof to an inside end thereof, and the first location of the path can be on the first side of the centerline disposed beyond the inside end.

The cutting surface can define a cutting direction toward the attachment portion, and the attachment portion can be configured to be receivable in an oscillating portion of the driver by application of a force to the saw blade in the cutting direction and removed therefrom by application of a force opposite the cutting direction of at least a threshold force. The threshold force can be greater than a first force sufficient for moving the instrument through a bone during operation thereof and less than a second force sufficient for moving the instrument through metal.

Another aspect of the present disclosure relates to a method for making a cut in a bone. The method includes positioning a cutting instrument with respect to a bone of a patient, the cutting instrument having an attachment portion proximal to a user and a cutting edge spaced distally of the attachment portion. At least a portion of the cutting edge is disposed toward the attachment portion, and the bone is positioned between the attachment portion and the cutting edge with a first side thereof disposed toward the attachment portion, and a second side thereof disposed toward the cutting edge. The method further includes drawing the cutting instrument in the proximal direction such that the cutting edge engages the second surface of the bone and cuts the bone while moving toward the first surface thereof.

The bone can be a proximal tibia, the first side of the bone can be an anterior side thereof, and the second side can be a posterior side thereof. Further, the bone can include at least a portion of an implanted device affixed thereto, and the cut can be made adjacent the implanted device for removal thereof from the bone.

The instrument can further include a body connecting the attachment portion and the cutting edge. The body can be at least partially disposed on a first side of an open area defined between the cutting edge and the attachment portion.

The step of positioning the instrument can be such that the body portion of the instrument is disposed outside the bone on a medial side thereof. Further, the step of drawing the instrument in the proximal direction can be such that the instrument cuts the bone through the medial side. Such a method can further include positioning the cutting instrument with respect to the bone such that the bone is positioned between the attachment portion and the cutting edge with a first side thereof disposed toward the attachment portion, and a second side thereof disposed toward the cutting edge and such that the body portion is disposed outside the bone on a lateral side thereof. The method can also further include drawing the cutting instrument in the proximal direction such that the cutting edge engages the second surface of the bone and cuts the bone while moving toward the first surface thereof to form a cut through the lateral side of the bone. The cutting edge can cut the bone by an oscillating movement thereof caused by the driver.

BRIEF DESCRIPTION OF THE DRAWINGS

A more complete appreciation of the subject matter of the present invention and the various advantages thereof can be realized by reference to the following detailed description in which reference is made to the accompanying drawings in which.

DETAILED DESCRIPTION

Figure 1:
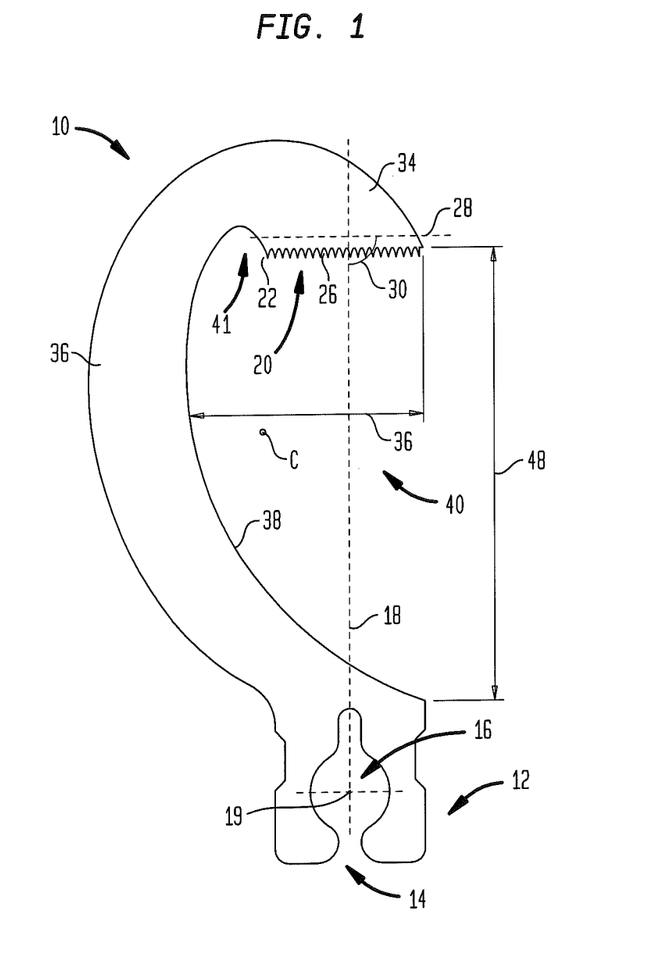
FIG. 1 is an orthopedic saw blade according to an embodiment of the present disclosure.

FIG. 1 shows a saw blade 10 according to an embodiment of the present disclosure. Blade 10 generally includes a base 12 and a cutting edge 20 remote from and facing the base 12. An arm 36 extends between base 12 and cutting edge 20 and is configured to position and support cutting edge 20 relative to base 12. In the embodiment shown, cutting edge 20 is positioned on a free end 34 of arm 36 and can be integrally formed with arm 36. Similarly, arm 36 can be integrally formed with base 12 such that blade 10 is of a unitary or monolithic structure that can have smooth transitions between the features discussed herein such that there is no definite boundary therebetween. For example, base 10 can transition smoothly to arm 36 or cutting edge 20 can be a sharpened or serrated edge of arm 36 such as on free end 34 thereof. Other embodiments are possible wherein the boundaries between the features are clearly defined, such as by being included on separate part of a blade assembly or the like.

Figure 2:
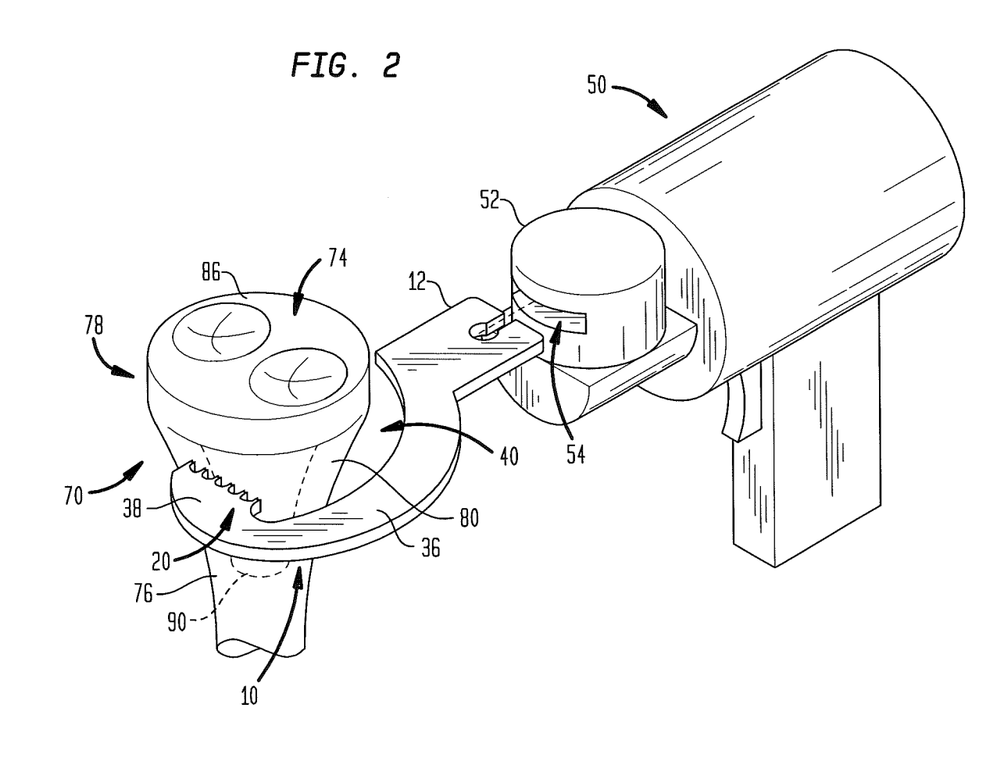
FIG. 2 is a first configuration of an assembly including the saw blade of FIG. 1 with a saw driver, the assembly shown in connection with a bone during a step in a method of use therewith.
Figure 3:
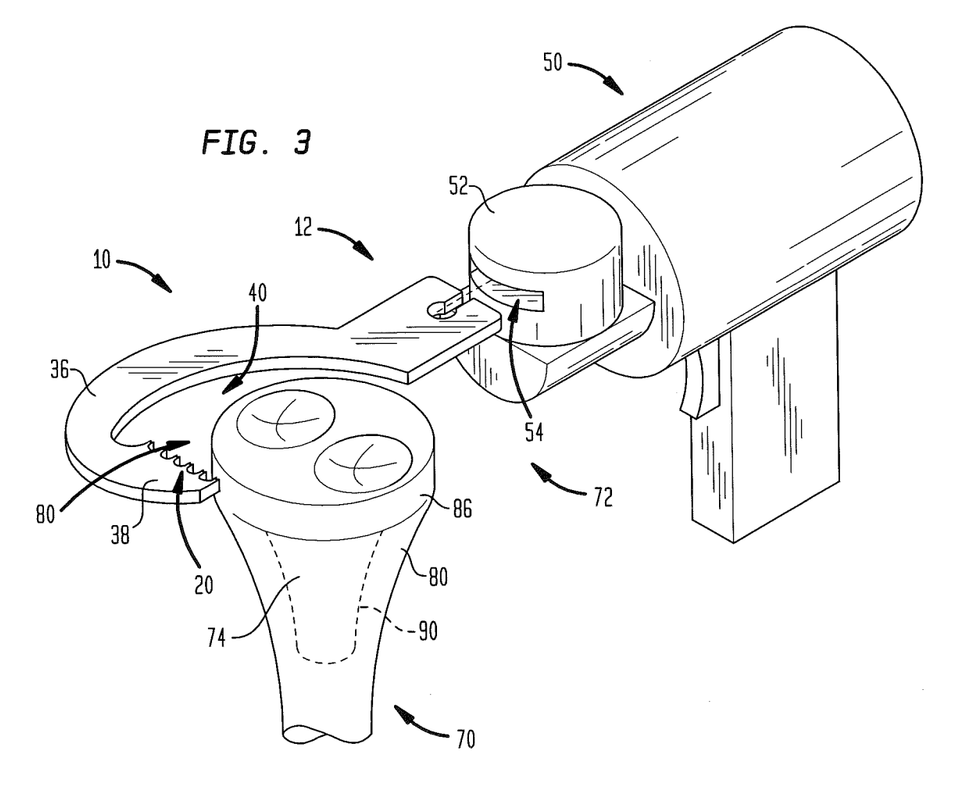
FIG. 3 is a second configuration of the assembly including the saw blade of FIG. 1 with a saw driver, the assembly shown in connection with a bone during another step in a method of use therewith.
Figure 4:
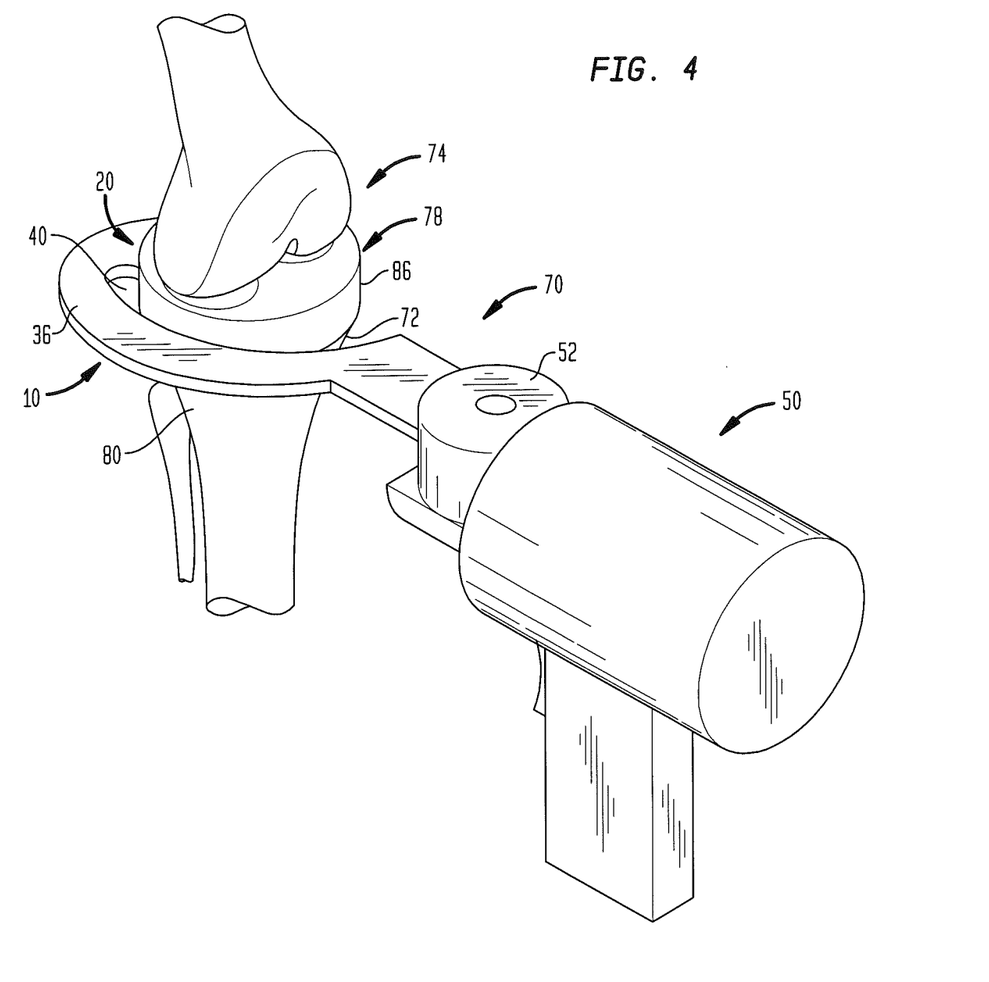
FIG. 4 is a rear view of the assembly configuration of FIG. 4 shown in connection with bones during a step in a method of use therewith.

Blade 10 can be configured to function as an oscillating saw blade that can be assembled with an oscillating saw driver unit, such as saw 50 shown in FIGS. 2-4. Such saws can function by securing a blade, such as blade 10, within a chuck 52 or other similarly-configured portion thereof. Saw 50 can be configured to drive chuck 52 in an oscillating motion about an axis. In an embodiment, the axis passes through chuck 52, such as through the center thereof such that when a blade is assembled therewith, the oscillation of chuck 52 causes the blade to rotate about a point that is located within the base 12 thereof. Other driving arrangements are possible for saws that can cause associated blades to move in different manners, and blades can be adapted to cut in response to such movement.

A number of different attachment configurations are possible to secure a blade within chuck 52. In some embodiments, the chuck can have internal features configured to grasp or mate with features of an associated blade. Blades and saws can be specially configured to work with each other, including having features of the blade that are sized and positioned to interact with matching features within the chuck to provide a snapping, press, clamping, or locking engagement therebetween. An example of a blade and saw combination with mutually engaging blade base and chuck features is the System 6™ oscillating saw and the collection of System 6™ blades available from Stryker® Orthopedics™.

A blade 10, including the base 12 thereof can be configured to work with such a saw and can further be adapted to work with other saws in a similar manner. In the embodiments shown, base 12 has a slot 14 therein that is open on an end thereof. The closed end of slot 14 includes a snap feature 16 that includes a portion thereof with a greater width than that of slot 14. In such an arrangement slot 14 can guide insertion of base 10 into a slot 54 within chuck 52 and snap feature 16 can accept a feature (not shown) within chuck 52 that can be, for example, spring loaded so as to move into and out of snap feature 16 in response to a pressure applied thereto. In the arrangement shown, blade 10 can be assembled into chuck 52 by aligning base 12 with slot 54 and applying a compressive force to blade 10. Similarly, blade 10 can be removed from chuck 52 by applying a tensile force to blade 10. The chuck 52 can be configured to require a predetermined threshold to be reached before permitting removal or insertion of blade 10 thereto. These forces can be the same or, for example, the removal threshold can be greater than the insertion threshold.

Arm 36 extends away from base 12 along a compound path to provide an open area 40 between base 12 and cutting edge 20. The compound path followed by arm 36 can extend in both a longitudinal direction and a lateral direction relative to the base 12. As shown in FIG. 1 a longitudinal axis 18 of blade 10 can extend from at or near the center of base 12 toward cutting edge 20. This axis can intersect the rotation point 19 for blade 10 and can further correspond with a center position of blade 10 along the oscillation path provided by saw 50. Longitudinal axis 18 defines a longitudinal direction in which arm 36 partially extends. A lateral direction, in which arm 36 also partially extends is perpendicular to longitudinal axis 18. The compound path along which arm 36 extends can, accordingly, be described as extending in the longitudinal direction to a position longitudinally remote from base 12 and extending in the lateral direction away from the longitudinal axis 18 and in the lateral direction back toward the longitudinal axis 18. In an embodiment, the arm can extend away from and back to the longitudinal axis 18. Such a path further defines the open area 40 as being bounded by at least base 12, cutting edge 20 and an inside edge 38 of arm 36 that follows the general path of arm 36 itself.

Open area 40 can be configured to receive a portion of a long bone of a patient therein. In the example shown in FIGS. 2-4, the long bone is a tibia 70 and open area 40 is configured to receive the proximal end of the tibia 70 therein. As shown open area 40 has a length in the longitudinal direction that is large enough to allow the base 12 to be on, for example, the anterior side 74 of the proximal tibia with the cutting edge 20 positioned over the posterior side 76 thereof. In such an arrangement, arm 36 can extend over either the medial 78 or lateral 80 side of the bone 70. As shown in FIGS. 2 and 3, blade 10 is configured to fit into chuck 52 of saw 50 in a first position (FIG. 2) with arm 36 on the lateral side 80 of the bone 70 and in a second position (FIG. 3) with arm 36 extending over the medial 78 side of the bone 70. The blade 10 can be changed between the positions by inversion along a longitudinal axis.

In the arrangement shown, blade 10 can be used with a driver 50 positioned over the anterior 74 side of the proximal tibia 70 to form a cut therein that originates on the posterior side 76 and extends toward the anterior side 74. This can be done by positioning the saw 50 and the blade 10 as shown in FIG. 1 and by drawing the saw 50 away from the bone. Such a cut can be made in at least two steps, one of which is made with blade 10 assembled with the saw 50 such that the arm 36 extends over the lateral side 80 of the bone to position the cutting edge over the posterior 76 of the bone laterally of a center thereof. This first step forms a cut extending from the posterior 76 of the bone 70 toward the anterior 74 thereof on the lateral side 80. The other of the at least two cuts can then be made with the blade 10 in the opposite position with respect to the bone 70, as shown in FIG. 3, such that the arm extends over the medial 78 side of the bone 70 to position the cutting edge 20 over the posterior 76 of the bone 70 medially of the center thereof. This can form a cut extending from the posterior 76 of the bone 70 toward the anterior 74 within the medial side 78 that can intersect with the cut along the lateral side 80 to form a single cut in the bone 70. In another embodiment, the medial cut can be made first with the lateral cut being made second and intersecting with the medial cut. In either embodiment, a plurality of cuts can be made on either side to achieve a desired result, depending on the shape, including the width of the bone, and the width of the cutting edge 20.

In the above-described embodiment, wherein blade 10 can be positioned with arm 36 extending on either side of a bone 70, the open area 40 can have a width 46 that is configured to accept only somewhat more than half of the designated bone, e.g. about 60% of the width of the bone. As shown, arm 36 has a rounded shape of a partial ellipse, oval, circle, or the like. Such a shape can define an open area 40 having a maximum lateral width 46 of between about 1.25" and 1.5" for a blade configured for use on a proximal tibia. In some embodiments, multiple blades of different sizes can be provided that can be selected to match the size and shape of a particular bone, for example a tibia or a femur. Blades with open areas of greater or smaller width can be used in connection with larger or smaller bones. Further, other shapes for arm 36 are possible, including more square shapes having defined sides thereof. The length 48 of open area 40 can be defined by the distance between base 12 and cutting edge 20. Such a length can be a maximum length in an arrangement with a rounded arm 36, such as that shown in the Figures. Length 48 can be between 1.75" and 2.25" for a blade 10 configured for use on a proximal tibia. In one embodiment, length 48 can be approximately 2". Other embodiments are possible wherein the length is larger or smaller as dictated by a particular bone for which the embodiment is intended.

Arm 36 can also be configured provide lateral clearance for cutting edge 20 during the oscillating motion implemented by saw 50. As shown in FIG. 1, a clearance portion 41 of open area 40 can be defined by a portion of arm 36 such that the clearance portion 41 provides an open space between the inside 22 of cutting edge 20 and the inside edge 38 of arm 36. The clearance portion 41 is defined by an adjacent portion of inside edge 38 of arm 36 that is appropriately shaped to be laterally spaced apart from inside 22 of cutting edge 20 at a distance at least to allow cutting edge 20 to move through a predetermined cutting path. The cutting path for cutting edge can vary based on the configuration of the cutting edge 20 itself, including based on the pitch (or spacing) of the teeth 26, the shape of the individual teeth 26, the number of teeth 26, among other factors. Such clearance can extend in a longitudinal direction past the leading portion of cutting edge 28 by a distance at least equal to, for example, the teeth 26 of cutting edge 20 or other cutting feature included thereon. In an embodiment, the clearance area 41 has a lateral width adjacent to the cutting edge 20 of between about 0.05" and 0.4". In another embodiment, the lateral width of clearance area 41, measured adjacent cutting edge 20, can have a width of about 0.25". Further, clearance area 41 can have a depth of at least 0.1". In another embodiment, clearance area 41 can have a maximum distance at a point therealong of at least about 0.12". This clearance area 41 can vary in size due to the size of the blade or configuration of the clearance area 41.

Arm 36 can further be configured to distribute the weight of blade 50 in a desired manner. For example, in an embodiment, arm can be configured such that the center of weight of blade 50 is at a location C, shown in FIG. 1, that is substantially laterally aligned with inside 22 of cutting edge 20 and is approximately near the longitudinal midpoint of blade 10. The weight distribution of blade 10 can be configured as such by adjusting the width of arm 36, including by giving arm 36 a variable width such that it is wider at at least a point therealong. Additionally, the weight distribution of blade 10 can be adjusted by increasing the size of the arm 36 near free end 34 thereof, including any portions thereof longitudinally past cutting edge 20. Such weight distribution can increase the cutting accuracy of the blade 10 and can reduce the vibration of blade 10 during use.

As discussed previously, cutting edge 20 is arranged so as to be disposed toward base 12. By way of example, this arrangement can be such that cutting edge 20 defines a portion of the boundary of open area 40. Further, cutting edge 20 can be positioned along a portion of arm 36, such as free end 34 thereof, such that the portion of arm 36 on which cutting edge 20 is positioned is spaced laterally away from base 12 relative to cutting edge 20. In a further example, the arrangement of cutting edge 20 can be such that a cutting direction defined by the cutting edge 20 is oriented generally toward base 12. A cutting direction of a cutting edge can be generally normal to the length of such cutting edge in a direction away from any supporting structure or body on which such cutting edge is formed.

In any of these arrangements, cutting edge 20 extends along a lateral axis 28 thereof positioned at an angle 30 relative to longitudinal axis 18. In the embodiments shown angle 30 is approximately 90°; however, in some embodiments, angle 30 can be between 75° and 105° and can further be between 85° and 95°.

Figure 5:
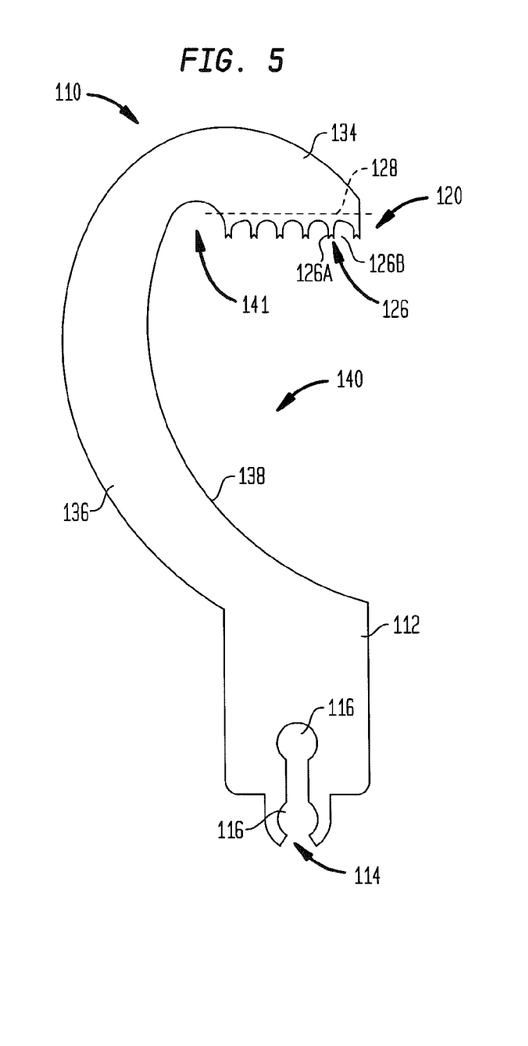
FIG. 5 is an orthopedic saw blade according to another embodiment of the present disclosure.
Figure 6:
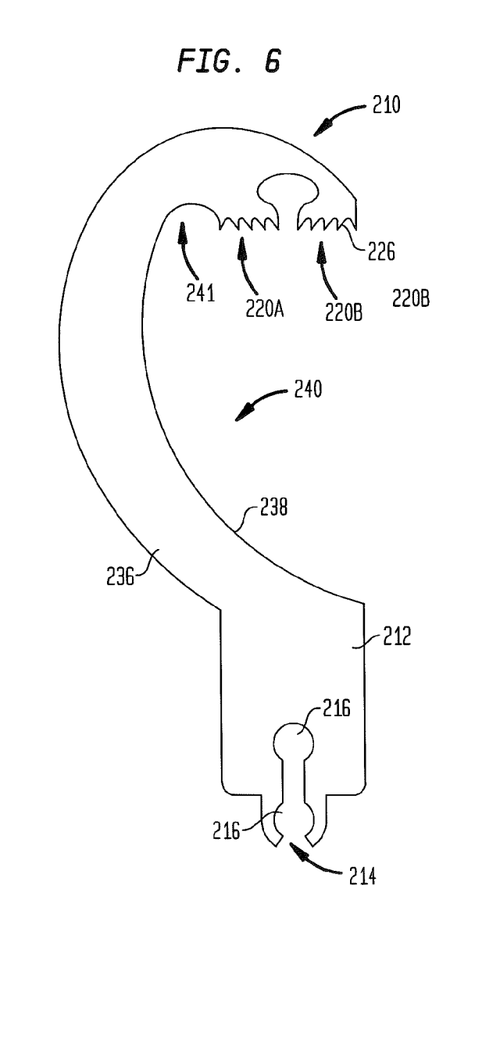
FIG. 6 is an orthopedic saw blade according to another embodiment of the present disclosure.
Figure 7:
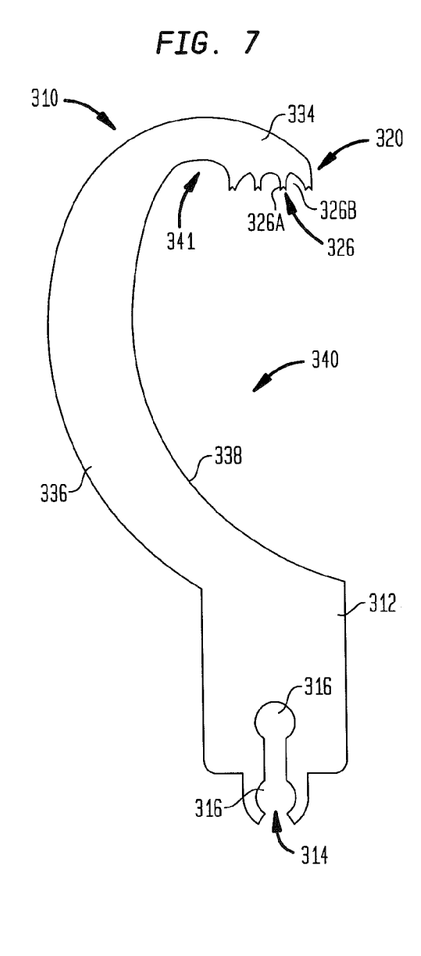
FIG. 7 is an orthopedic saw blade according to another embodiment of the present disclosure.
Figure 8:
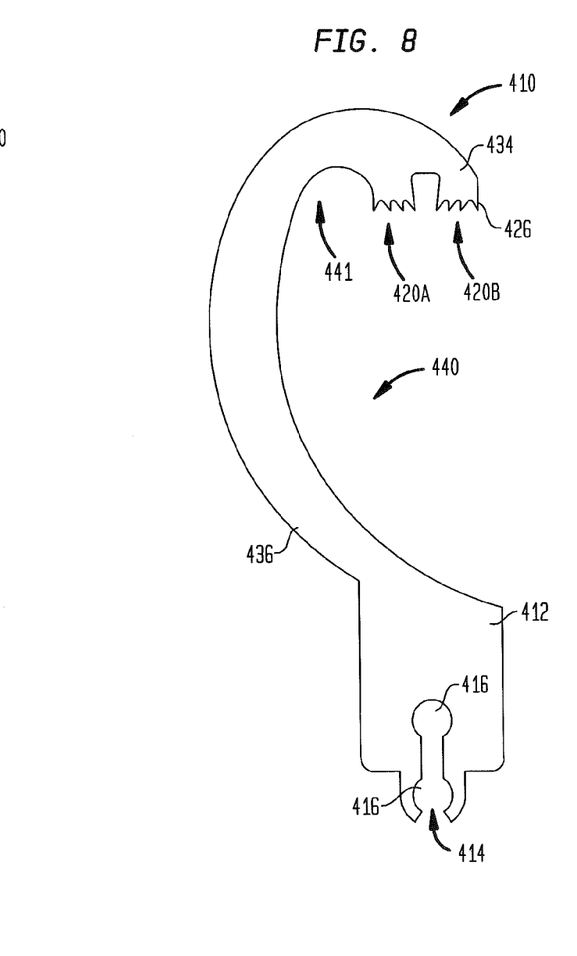
FIG. 8 is an orthopedic saw blade according to another embodiment of the present disclosure.

Teeth 26 are included in and can at least partially define cutting edge 20. A number of different arrangements for teeth 26 are possible and can be in any suitable configuration or arrangement for cutting bone. As shown in FIGS. 1-4, teeth 26 can be in a generally triangular configuration in which they are individually symmetrical and are substantially uniform along the lateral axis? axis 28 of cutting edge 20. Other arrangements for the teeth are shown in FIGS. 5-8. FIG. 5 shows an arrangement in which teeth 126 are forked at the ends thereof to form two end segments 126A and 126B on each individual tooth 126. Such teeth 126 can be symmetrical and evenly spaced along the longitudinal axis 128. FIG. 7 shows a similar arrangement in which cutting edge 320 is narrower than in other embodiments and includes fewer teeth 326. Such a cutting edge 320 can be used to cut, for example, a tibia. FIG. 6 shows a blade 210 in which cutting edge 220 is split into at least two segments 220A and 220B, each segment 220A,220B including teeth 226 that are asymmetrical and are oriented toward the center of the cutting edge 220. FIG. 8 shows a similar arrangement to that of FIG. 6, but with a narrower overall width for cutting edge 420, which also includes fewer teeth 426 in an arrangement for cutting a bone such as a femur.

Blade 10 can be made from a number of different materials including steel of various compositions such as medical grade stainless steel. Further, blade 10 can be made from titanium or various titanium alloys. The blade may also be coated in various materials to strengthen the overall blade. In some embodiments, cutting edge 20 can be of a different material than arm 36 or base 12. For example, base 12 and arm 36 can be made from steel and cutting edge 20 can be made from titanium or the like. In other embodiments, blade 20 can be made from a different type of steel than arm 36 or base 12 and can be integrally formed therewith such as by certain molding procedures or by welding. For example, blade 20 can be made from a relatively hard steel and arm 36 or base 12 can be made from a relatively soft steel. In other embodiments, cutting edge 20 and arm 36 can be of the same material with 20 having a treatment applied thereto. For example, edge 20 can be annealed or can have a carbide layer formed thereon.

Blade 10 can have a uniform thickness throughout its structure. Such a thickness can vary depending on the material that comprises blade 10, but can generally vary between about 0.025" and 0.075". In an embodiment, the thickness of blade 10 can be about 0.05". In an embodiment, cutting edge 20 can have a thickness that tapers toward a leading edge thereof or can have teeth 26 that have a thickness less than the uniform thickness of the remainder of blade 10. Further, portions of arm 36 near teeth 26 or other portions of cutting edge 20 can have geometry including somewhat thinner portions. Additionally, certain areas, of blade 10, such as base 12 or an area near the interface of base 12 and arm 36 can be thickened to reinforce the structure of blade 10.

Blades of the types shown and described herein can be used in the removal of worn or damaged implants during arthroplasty revision procedures. In the exemplary embodiment shown in FIGS. 2-4, blade 10 is shown in configurations thereof with saw 50 during various steps of a tibial revision procedure. In particular, the procedure is one in which an implant 86 is to be removed from the tibial plateau so that it can be replaced with a new implant. Implant 86 is of an exemplary configuration shown to illustrate a use of a blade in various embodiments disclosed herein, the general concepts of such use being applicable to implants of other configurations. In particular implant 86 includes an anchoring feature in the form of a keel 90 that protrudes beneath the resected surface of the tibia on which implant 86 rests and into the cancellous portion of the bone. Other anchoring features are possible, including multiple posts of varying depths or the like. Blade 10 can be used in such a revision procedure to form a cut in bone 70 immediately below implant 86 or at the interface therebetween in an area disposed to the posterior of keel 90 (or other anchoring feature) with saw 50 disposed on the anterior side of the bone 70. Such a cut can be used in connection with a cut formed from the anterior side of bone 70 and extending toward the posterior side made using a straight bone saw on the anterior side of the bone. By using two such cuts made with blade 10 and a straight saw blade, the entire implant 86 can be loosened from an approach taken on a single side of the bone 70, such as the anterior side 74. Such a procedure can allow for a smaller incision and/or the use of fewer retraction configurations of the soft tissue surrounding the bone 70 compared to revision procedures wherein the implant is loosened using only a straight saw blade.

An embodiment of a method for removing an implant, such as implant 86 can use a blade, such as blade 10, according to the various embodiments thereof discussed herein. Such a method can include gaining access to the proximal tibia 70 (or other bone, depending on the procedure) through an incision and retracting the soft tissue surrounding the implant 86 to expose the anterior side 74 of the proximal tibia 70. A straight saw can then be used to form a cut or multiple cuts starting from the anterior side 74 of the bone 70 that can extend toward the posterior side 76 of the bone 70. In some areas the straight saw will not obstructed by keel 90 or other such feature. In other locations, however, keel 90 can prevent the cut from extending through the portion of bone located on the posterior side of keel 90. Such portions of the bone 70 can be cut by removing the straight saw from the prepared area and from saw 50 and by assembling blade 10 with saw 50, as described above, in the orientation shown in FIGS. 2 and 4. The saw 50 is then positioned such that cutting edge is positioned over the posterior side 76 of the bone 70 with arm 36 extending around bone 70 and around keel 90 and through the incision to the anterior side 74 of the bone 70. A cut is then made in the area of bone 70 posterior to keel 90 by activating the saw 50 and moving the saw 50 away from the bone (or in an anterior direction relative to the bone). Multiple cuts can be made, as needed to appropriately loosen the implant 86. Further, blade 10 can be removed from the prepared area and from saw 50 and then repositioned as shown in FIG. 3. This assembly can then be used to make a cut (or multiple cuts) in the area of bone 70 posterior to keel 90 on an opposite medial-lateral side from previous cuts made with blade 10 in the configuration of FIG. 2. Such a step may be used depending on the geometry of the bone, the implant, and the particular blade 10 used. A similar method can be carried out on other bones to remove differently-configured implants having similar or different anchoring features. Such a method can use a blade 10, as shown in FIGS. 1-4 or other blades as shown in FIGS. 5-8. For example, a similar method can be used to remove a worn or damaged femoral head implant using a blade 320 or 420 as shown respectively in FIGS. 7 and 8. Any of these procedures can be carried out using an anterior approach, as discussed above, or using other approaches, such as from the lateral, medial, or posterior sides of the bone. Such approaches can be carried out in a similar manner to those discussed above.

Figure 9:
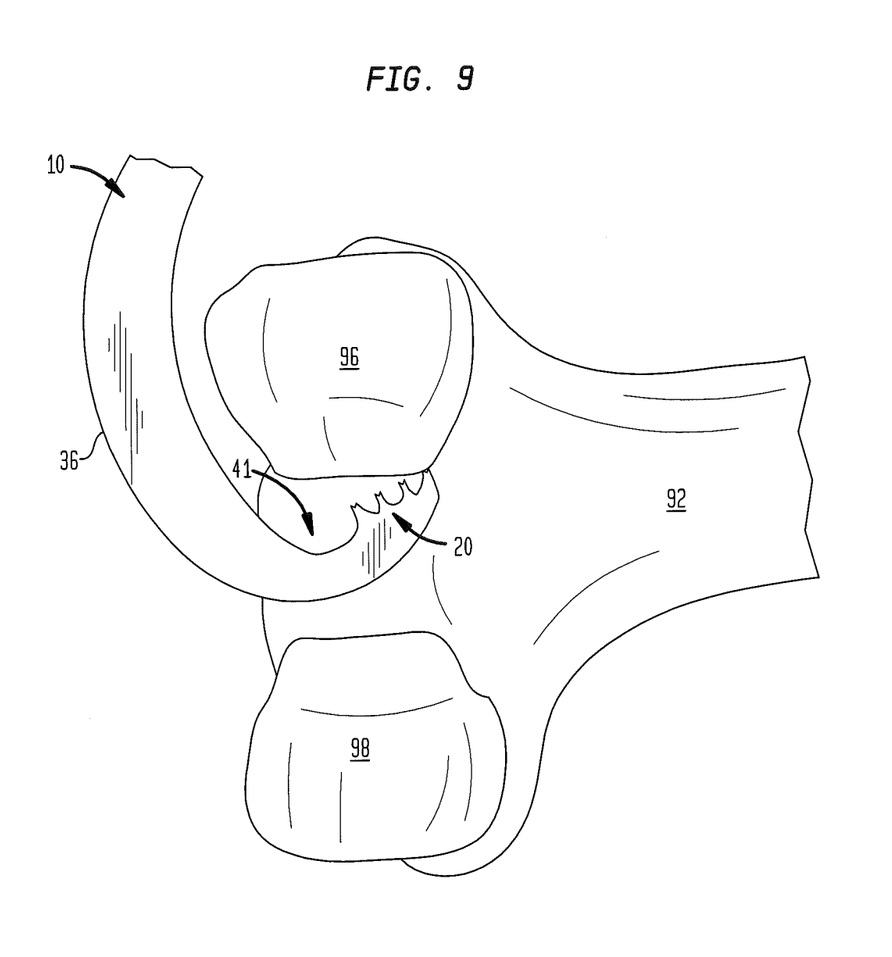
FIG. 9 is the orthopedic saw blade shown in connection with a bone during a step in a method of use thereof.

In a further method embodiment, a blade 10 of any of the types shown herein can be used in a further aspect of a knee revision procedure including resection of a worn or damaged distal femoral implant. As shown in FIG. 9, blade 10 can be positioned with one of the femoral condyles 96 or 98 within open area 40 of blade 10. This can allow cutting edge 20 of blade to be positioned either on an interior side of the condyle 96, as shown in FIG. 9 or on the posterior side of the condyle 96. As in the proximal tibial revision method discussed above, access to the medial and anterior portions of the condyle can be gained by an anterior approach in which arm 36 of blade 10 can pass through an anterior incision. In such a method, blade 10 can be used to loosen the distal femoral implant along the interior side of the condyle 96 or 98 by moving blade 10 away from the interior portion of the bone (either medially or laterally, depending on the side of the condyle), as permitted by the clearance area 41 of blade 10. Further, the implant can also be loosened along the posterior side of either condyles 96 or 98 by positioning the cutting edge 20 adjacent thereto and drawing the blade 10 in an anterior direction. Loosening of the implant can include a number of cuts originating, as described, from the interior side and the posterior side of both condyles 96 and 98 and can further include cuts made at an angle or taking compound paths, as determined necessary by the user of the blade 10.

As discussed above, the configuration of base 12 shown in connection with blade 10 can allow blade 10 to be removed from chuck 52 of saw 50 by application of a tensile force to blade 10. In the methods described herein, the force used to move saw 50 through the bone 70 to make the desired cut or cuts also applies a tensile force to blade 10. In such embodiments, the chuck 52 and base 12 can be mutually configured such that the threshold force for removal of blade 12 is greater than a force necessary to make the desired cuts. Such a removal force can further be configured to be generally less than a force that would be applied to blade 10 to cut through metal. In such an arrangement, blade 10 can, thusly, be configured to become dislodged from chuck 52 should it be forced into contact with a metal feature, such as keel 90. Such a configuration can prevent damage to blade 10, implant 86 or the surround bone and tissue of the patient.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A saw blade for cutting bone including a base portion configured for attachment with a driver, the saw blade comprising:
 a body portion including an inside edge and having a length extending from the base portion to a free end of the body portion, the body portion enclosing at least part of an open area adjacent the base portion; and
 a cutting edge having a width and disposed on the body portion at an end surface on the free end thereof, the end surface adjoining the inside edge and adjacent to the open area such that at least a portion of the cutting edge is disposed toward the base portion; and
 wherein the inside edge includes a first inside edge portion and a second inside edge portion, the first inside edge portion extending from the cutting edge to an apex further from the base portion than the cutting edge and from the apex to a first point closer to the base portion than the cutting edge, and the second inside edge portion extending from the first point to the base portion.

2. The saw blade of claim 1, wherein a first axis extending through the width of the cutting edge, and extending parallel to the end surface, intersects a second axis extending through a center of rotation in the base portion and the end surface, wherein the first axis is disposed at a first angle relative to the second axis, the first angle being between 75° and 105°.

3. The saw blade of claim 2, wherein the first axis extends from the width of the cutting edge through the open area to the inside edge.

4. The saw blade of claim 3, wherein the cutting edge includes a plurality of teeth having substantially equal widths and spaced apart along the width of the cutting edge.

5. The saw blade of claim 3, wherein a length of the first axis through the open area defines a first distance, wherein the first distance is at least about 0.25 inches.

6. The saw blade of claim 2, wherein the first angle is about 90°.

7. The saw blade of claim 1, wherein the base portion defines a center of rotation for the blade, and wherein the cutting edge extends along a lateral axis that is tangent to an arc centered at the center of rotation.

8. The saw blade of claim 1, wherein the body portion of the saw blade includes an outside edge, wherein at least a portion of the outside edge is curved.

9. The saw blade of claim 1, wherein an axis extending through a center of rotation of the base portion defines a centerline extending in a first direction, and wherein a longitudinal axis of the body portion extends away from the base portion at an angle relative to the centerline of the base portion along an arced path from the base portion toward a first location remote therefrom and from the first location toward the free end such that the longitudinal axis from the first location toward the free end approaches the centerline.

10. The saw blade of claim 9, wherein the cutting edge extends away from the centerline on a first side thereof to an inside end thereof, and wherein the first location on the longitudinal axis of the body portion is on the first side of the centerline and is disposed at a distance from the inside end.

11. The saw blade of claim 10, wherein the first location is located at a distance of at least 1 inch from the inside end.

12. The saw blade of claim 1, wherein the open area is sized to receive a portion of a long bone therein.

13. The saw blade of claim 1, wherein the cutting edge defines a cutting direction toward an attachment portion of the base portion, and wherein the attachment portion is configured to be receivable in an oscillating portion of the driver by application of a force to the saw blade in the cutting direction and removed therefrom by application of a force opposite the cutting direction of at least a threshold force.

14. The saw blade of claim 13, wherein the threshold force is greater than a force sufficient for moving the saw blade through a tibia or a femoral condyle during operation thereof.

15. A saw blade for cutting bone including a base portion configured for attachment with a driver, the saw blade comprising:
- a body portion including an inside edge and an outside edge and having a length extending from the base portion to a free end of the body portion, the body portion enclosing at least part of an open area adjacent the base portion; and
- a cutting edge having a width extending from the inside edge to the outside edge and disposed on the body at the free end thereof and adjacent to the open area such that at least a portion of the cutting edge is disposed toward the base portion,
- wherein the inside edge includes a first curve with a first radius and the outside edge includes a second curve with a second radius, each of the first and second curves having a center external to the body in the open area side of the body, and
- wherein at least a portion of the first curve of the inside edge and at least a portion of the second curve of the outside edge include a common radius of curvature.

16. A saw blade for cutting bone including a base portion configured for attachment with a driver, the saw blade comprising:
- a body portion having a length extending from the base portion to a free end of the body portion, the body portion enclosing at least part of an open area adjacent the base portion; and
- a cutting edge disposed on an end surface on the free end of the body portion, the end surface extending from an inside edge of the body to an outside edge of the body and adjacent to the open area such that at least a portion of the cutting edge is disposed toward the base portion; and
- wherein the cutting edge is orthogonal to an axis passing through the cutting edge and a center of rotation of the base portion.

* * * * *